United States Patent
Behner et al.

[11] 3,936,463
[45] Feb. 3, 1976

[54] BENZOMORPHANES

[75] Inventors: Otto Behner; Ulrich Horlein; Friedrich Hoffmeister; Hans Werner Schubert, all of Wuppertal, Germany

[73] Assignee: Bayer Aktiengesellschaft, Germany

[22] Filed: Dec. 3, 1973

[21] Appl. No.: 421,439

[30] Foreign Application Priority Data
Dec. 7, 1972 Germany............................ 2259979

[52] U.S. Cl. ...... 260/293.54; 260/DIG. 13; 424/267
[51] Int. Cl.². ....................................... C07D 221/26
[58] Field of Search................. 260/293.54, DIG. 13

[56] References Cited
UNITED STATES PATENTS
3,733,330  5/1973  Schubert et al................ 260/293.54

*Primary Examiner*—G. Thomas Todd

[57] ABSTRACT

Benzomorphanes of the formula:

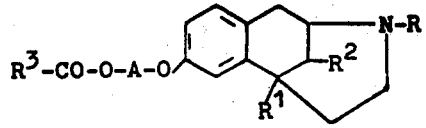

wherein
R is cyclopropylmethyl or cyclobutylmethyl;
$R^1$ and $R^2$ are the same or different and each is lower alkyl;
$R^3$ is hydrogen; a straight, branched or cyclic, saturated, partially unsaturated or unsaturated aliphatic hydrocarbon unsubstituted or substituted by 1 or more substituents selected from the group consisting of lower alkoxy, lower alkoxycarbonyl, lower alkylmercapto, aryloxy, arylmercapto, arylamino, and an acid amide; an unsubstituted or substituted aromatic moiety; an unsubstituted or substituted 5-, 6- or 7-membered heterocyclic ring; lower alkylamino; di(lower alkyl)amino; arylamino; lower alkyl-arylamino; lower alkoxy; urethane; an acid amide; lower alkoxycarbonylamino; or lower alkoxycarbonyl-lower alkylamino; and
A is a bivalent, straight- or branched-chain, saturated, partially unsaturated or unsaturated hydrocarbon of 2 to 10 carbon atoms, unsubstituted or substituted by phenyl or by phenyl substituted by at least 1 substituent selected from the group consisting of lower alkyl, lower alkoxy, nitro, amino and halogen, and pharmaceutically acceptable nontoxic salts thereof, are useful as analgesics.

25 Claims, No Drawings

BENZOMORPHANES

The present invention relates to benzomorphanes, to their production, to analgesic compositions wherein said benzomorphanes are the active agent and to methods of effecting analgesia in humans and animals which comprises administering the benzomorphanes of the present invention to such humans or animals.

It is known in the art that benzomorphan derivatives exhibit analgesic activity.

It has already been disclosed that benzomorphan derivatives can be powerful analgesics. In recent years, very many patents have appeared in this field, for example Belgian Patent 680,526 (1965). J. R. Geigy AG; Belgian Pat. No. 721,890 (1968), Grelan Pharm. Co. Ltd.; U.S. Pat. No. 3,382,249 (1964), Sterling Drug Inc.; Belgian Pat. No. 750,484 (1969), Bayer AG.

Most of the powerful analgesics known at the present time have qualitatively the same action as morphine. They also exhibit the same side effects as morphine. Outstanding among these side-effects is their capacity to cause physical and psychological dependence. Any substance having a powerful analgesic action, which in comparison to substances having a morphine-like action does not possess a pronounced addiction or dependence potential would represent a considerable advance (WHO Technical Report Series 1972, No. 495).

It has recently been found that substances which in addition to morphine-like effects also have morphine-antagonistic properties can also be powerful analgesics, their addition potential being substantially less than that of the compounds which only have a morphine-like action. However, the applicability of these compounds is also restricted by other psychological side-effects inherent in these compounds, such as dysphoria and hallucinations (WHO Technical Report Series 1972, No.495). For this reason it is desirable to develop new therapeutic agents which do not show the morphine-like characteristic side-effects and which also do not have the psychological side-effects of the morphine-antagonistic substances.

More particularly, the present invention is concerned with benzomorphan derivatives of the formula:

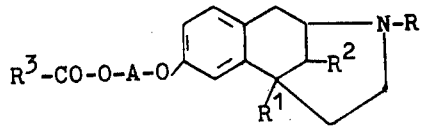

and pharmaceutically acceptable nontoxic salts thereof wherein

R is cyclopropylmethyl or cyclobutylmethyl;

$R^1$ and $R^2$ are the same or different and each is lower alkyl;

$R^3$ is hydrogen; a straight, branched or cyclic, saturated, partially unsaturated or unsaturated aliphatic hydrocarbon particularly of up to 11 carbon atoms, preferably alkyl of 1 to 11 carbon atoms or alkenyl of 2 to 11 carbon atoms, unsubstituted or substituted by 1 or more, preferably 1 or 2, and particularly 1, substituent selected from the group consisting of alkoxy of 1 to 4 carbon atoms, especially 1 or 2 carbon atoms, alkoxycarbonyl of 1 to 4 carbon atoms in the alkoxy moiety, and particularly of 1 or 2 carbon atoms in the alkoxy moiety, alkylmercapto of 1 to 4 carbon atoms, and especially of 1 or 2 carbon atoms, aryloxy, especially phenoxy, arylmercapto, especially phenylmercapto, arylamino, especially phenylamino, and an acid amide; an unsubstituted or substituted aromatic moiety particularly of 6 to 10 carbon atoms, especially phenyl or salicyl; an unsubstituted or substituted 5-, 6- or 7-membered heterocyclic ring, especially nicotinyl; lower alkylamino, especially alkylamino of 1 to 4 carbon atoms, and particularly 1 or 2 carbon atoms; di(lower alkyl)amino, particularly dialkylamino of 1 to 4 carbon atoms, and especially 1 or 2 carbon atoms in each alkyl moiety; arylamino, especially phenylamino; lower alkyl-arylamino, especially alkylphenylamino of 1 to 4 carbon atoms in the alkyl moiety; lower alkoxy, particularly of 1 to 4 carbon atoms, and especially of 1 or 2 carbon atoms; urethane; an acid amide; alkoxycarbonylamino, especially of 1 to 4 carbon atoms in the alkoxy moiety; or alkoxycarbonylalkylamino, especially of 1 to 4 carbon atoms in the alkoxy moiety, and of 1 to 4 carbon atoms in the alkyl moiety, and particularly of 1 or 2 carbon atoms in the alkyl moiety, and particularly of 1 or 2 carbon atoms in the alkoxy moiety and 1 or 2 carbon atoms in the alkyl moiety; and A is a bivalent, straight- or branched-chain, saturated, partially unsaturated or unsaturated hydrocarbon of 2 to 10 carbon atoms, particularly alkylene or alkylidene of 2 to 7 carbon atoms unsubstituted or substituted by phenyl or by phenyl substituted by at least 1, and preferably 1, substituent selected from the group consisting of lower alkyl, and especially alkyl of 1 to 4 carbon atoms, lower alkoxy, and especially alkoxy of 1 to 4 carbon atoms, nitro, amino and halogen, especially chlorine or bromine.

The terms "lower alkyl", "lower alkoxy", "lower alkylamino" and "di(lower alkyl)amino" mean that the alkyl and alkoxy moieties have from 1 to 5 carbon atoms.

The benzomorphanes of the present invention are produced by:

a. reacting a benzomorphan of the formula

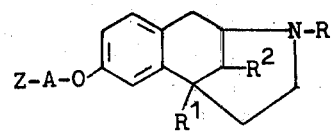

wherein R, $R^1$, $R^2$ and A are as above defined and Z is hydroxy or halogen, with a compound of the formula
$$R^3-Y \qquad \text{III}$$
wherein $R^3$ is as above defined and Y is -NCO or -COX, wherein X is hydroxy, lower alkoxy, aryloxy, especially phenoxy, acyloxy or halogen, preferably at a temperature between $-10°$ C and $+180°$ C. either in the presence or the absence of an acid-binding agent;

b. reacting a benzomorphan of the formula

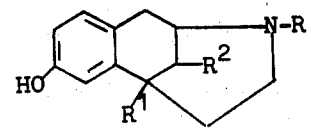

or a metal salt thereof, wherein R, $R^1$ and $R^2$ are as above defined, with a reactive ester, preferably a halide, a formic acid ester or a sulphonic acid ester, of a hydroxy compound of the formula
$$R^3-CO-O-A-OH \qquad V$$
wherein $R^3$ and A are as above defined, in the presence of an acid-binding agent except that where the benzomorphan is in the form of a metal salt, in which case the acid-binding agent is not used; preferably at a temperature of between —10°C and +120°C; or c. reacting a benzomorphan of the formula

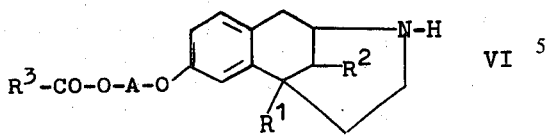

wherein $R^1$, $R^2$, $R^3$ and A are as above defined, with a reactive ester, preferably a halide, a formic acid ester, or a sulphonic acid ester, of a hydroxy compound of the formula

R — OH  VII wherein R is as above defined, either in the presence or the absence of an acid-binding agent, preferably at a temperature between —10°C and +150°C.

The three processes (a), (b) and (c) set forth above are hereinafter referred to as Process Variants (a), (b) and (c) respectively.

It was surprisingly found that the compounds of the present invention exhibit a more powerful analgesic effect than most known benzomorphanes, are better tolerated than most benzomorphanes, and, further, have not been shown according to our work done to date to be addictive.

According to one embodiment of the present invention $R^3$ is hydrogen; straight- or branched-chain alkyl of 1 to 11 carbon atoms, straight- or branched-chain alkenyl of 2 to 11 carbon atoms or cycloalkyl of 3 to 6 carbon atoms, unsubstituted or substituted by 1 or 2 members selected from the group consisting of alkoxy of 1 or 2 carbon atoms, alkoxycarbonyl of 1 or 2 carbon atoms in the alkoxy moiety, alkylmercapto of 1 or 2 carbon atoms in the alkyl moiety, phenoxy, phenylmercapto and phenylamine; phenyl unsubstituted or substituted by hydroxy; nicotinyl; alkylamino of 1 or 2 carbon atoms in the alkyl moiety; dialkylamino of 1 or 2 carbon atoms in each alkyl moiety; phenylamino; alkylphenylamino of 1 to 4 carbon atoms in the alkyl moiety; alkoxy of 1 or 2 carbon atoms; urethane; alkoxycarbonylamino of 1 to 4 carbon atoms in the alkoxy moiety; or alkoxycarbonyl-alkylamino of 1 or 2 carbon atoms in the alkoxy moiety and 1 or 2 carbon atoms in the alkyl moiety; and A is alkylene or alkylidine of 2 to 7 carbon atoms, unsubstituted or substituted by phenyl or by phenyl substituted by alkyl of 1 or 2 carbon atoms, alkoxy of 1 or 2 carbon atoms, nitro, amino or halogen.

According to another embodiment of the present invention $R^1$ and $R^2$ are the same or different and each is methyl or ethyl;

$R^3$ is straight- or branched-chain alkyl of 1 to 11 carbon atoms, straight- or branched-chain alkenyl of 2 to 11 carbon atoms or cycloalkyl of 3 to 6 carbon atoms, unsubstituted or substituted by a member selected from the group consisting of alkoxy of 1 to 4 carbon atoms, alkoxycarbonyl of 1 to 4 carbon atoms in the alkyl moiety, alkylmercapto of 1 to 4 carbon atoms, phenoxy, phenylmercapto, alkoxycarbonylamino of 1 to 4 carbon atoms in the alkoxy moiety, and alkoxycarbonyl-alkylamino of 1 to 4 carbon atoms in the alkoxy moiety and of 1 to 4 carbon atoms in the alkyl moiety; phenyl or pyridyl unsubstituted or substituted by a member selected from the group consisting of hydroxy, alkyl of 1 to 4 carbon atoms, alkoxy of 1 to 4 carbon atoms and alkylamino of 1 to 4 carbon atoms; alkylamino of 1 to 4 carbon atoms; dialkylamino of 1 to 4 carbon atoms; phenylamino; alkylphenylamino of 1 to 4 carbon atoms in the alkyl moiety; alkoxy of 1 to 4 carbon atoms; urethane; alkoxycarbonylamino of 1 to 4 carbon atoms in the alkoxy moiety; or alkoxycarbonyl-alkylamino of 1 to 4 carbon atoms in the alkyl moiety and 1 to 4 carbon atoms in the alkoxy moiety; and A is alkylene or alkylidene of 2 to 10 carbon atoms, preferably 2 to 7 carbon atoms, unsubstituted or substituted by phenyl or by phenyl substituted by alkyl of 1 to 4 carbon atoms, alkoxy of 1 to 4 carbon atoms, chlorine or bromine. According to another embodiment of the present invention $R^1$ and $R^2$ are the same or different and each is methyl or ethyl;

$R^3$ is straight- or branched-chain alkyl of 1 to 6 carbon atoms, straight- or branched-chain alkenyl of 2 to 6 carbon atoms or cycloalkyl of 3 to 6 carbon atoms unsubstituted or substituted by alkoxy of 1 to 4 carbon atoms, alkoxycarbonyl of 1 to 4 carbon atoms in the alkoxy moiety, alkylmercapto of 1 to 4 carbon atoms in the alkyl moiety, phenoxy, phenylmercapto, alkoxycarbonylamino of 1 to 4 carbon atoms in the alkoxy moiety and alkoxycarbonyl-alkylamino of 1 or 2 carbon atoms in the alkoxy moiety and 1 or 2 carbon atoms in the alkyl moiety; phenyl or pyridyl unsubstituted or substituted by hydroxy, alkyl of 1 or 2 carbon atoms, alkoxy of 1 or 2 carbon atoms or alkylamino of 1 or 2 carbon atoms; alkylamino of 1 or 2 carbon atoms, dialkylamino of 1 or 2 carbon atoms in each alkyl moiety; phenylamino; alkylphenylamino of 1 or 2 carbon atoms in the alkyl moiety; alkoxy of 1 or 2 carbon atoms, urethane; alkoxycarbonyl-alkylamino of 1 or 2 carbon atoms in the alkoxy moiety; or alkoxycarbonyl-alkylamino of 1 or 2 carbon atoms in the alkoxy moiety and 1 or 2 carbon atoms in the alkyl moiety; and A is alkylene or alkylidene of 2 to 7 carbon atoms unsubstituted or substituted by phenyl or by phenyl substituted by alkyl of 1 or 2 carbon atoms, alkoxy of 1 or 2 carbon atoms, chlorine or bromine. According to another embodiment of the present invention $R^1$ and $R^2$ are the same or different and each is methyl or ethyl;

$R^3$ is straight- or branched-chain alkyl of 1 to 11 carbon atoms; straight- or branched-chain alkenyl of 2 to 6 carbon atoms; phenyl; salicyl; nicotinyl; alkylamino of 1 or 2 carbon atoms; dialkylamino of 1 or 2 carbon atoms; phenylamino; alkoxy of 1 or 2 carbon atoms or alkoxycarbonyl-alkylamino of 1 or 2 carbon atoms in the alkoxy moiety and 1 or 2 carbon atoms in the alkyl moiety; and A is alkylene or alkylidene of 3 to 7 carbon atoms.

According to another embodiment of the present invention $R^1$ is methyl or ethyl;

$R^2$ is methyl;

$R^3$ is methyl; ethyl; propyl; butyl; undecyl; ethoxymethyl; ethoxycarbonylethyl; allyl; decenyl; phenyl; salicyl; phenoxymethy; phenylamino; nicotinyl; ethoxy; ethylamino; dimethylamino; or ethoxycarbonylmethylamide; and A is propylene; butylene; pentylene; methylpropylene; dimethylethylene; methylbutylene; methylpentylene; or isopropylbutylene.

X is preferably hydroxy, alkoxy of 1 to 10 and especially 1 to 6 carbon atoms, phenoxy, acyloxy wherein the acyl portion preferably is formyl, or $R^3CO$ wherein $R^3$ is above defined, or halogen, especially chlorine or bromine.

According to the present invention, the preferred salts of the benzomorphanes of the present invention include the hydrohalides, especially the hydrochloride, the sulphates, phosphates, tartrates, citrates and naphthalene-1,5-disulphonates. The hydrochloride salt and the naphthalene-1,5-disulphonate salt are particularly preferred.

If 2-cyclopropylmethyl-5,9-dimethyl-2'-[3-hydroxypropoxy-(1)]-6,7-benzomorphan and propionic anhydride are used as starting compounds, the course of the reaction for Process Variant (a) can be represented by the following equation:

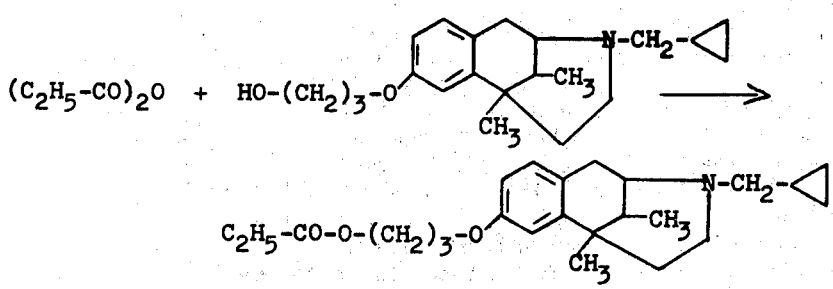

while if 2-cyclopropylmethyl-5-ethyl-9-methyl-2'-[3-bromopropoxy-(1)]-6,7-benzomorphan and salicylic acid are used as starting compounds, the course of the reaction can be represented by the following equation:

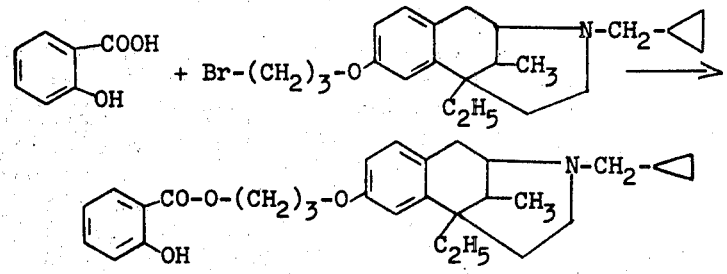

If the sodium salt of 2-cyclobutylmethyl-5-ethyl-9-methyl-2'-hydroxy-6,7-benzomorphan and 3-acetoxypropyl-1-bromide are used as starting compounds, the course of the reaction for Process Variant (b) can be represented by the following equation:

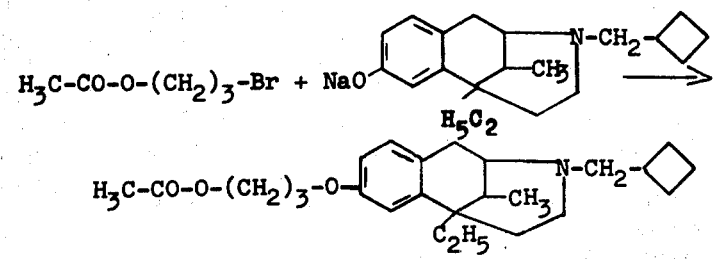

If 5-ethyl-9-methyl-2'-[3-acetoxypropoxy-(1)]-6,7-benzomorphan and cyclobutylmethyl bromide are used as starting compounds, the course of the reaction for Process Variant (c) can be represented by the following equation:

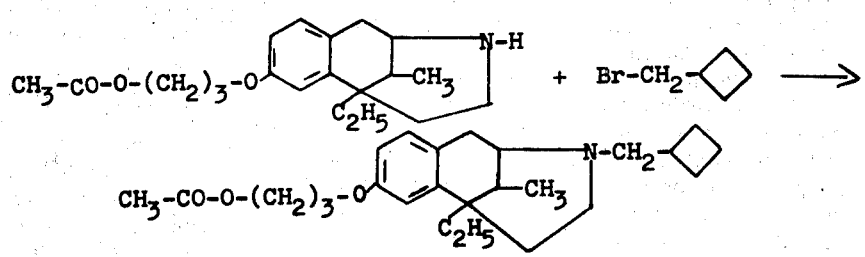

The benzomorphanes of the general formula II which can be used as starting compounds in Process Variant (a) according to the invention are already known or can be produced by known methods (DOS (German Published Specification) 1,925,296).

The starting compounds used in the process according to the invention of the general formulae III, IV, V and VII are either already known or can be produced by known methods. The individual substituent groups of these compounds preferably have the meaning already mentioned above.

The compounds of the general formula VI which are used as the starting compounds in Process Variant (c)

according to the invention are not known but can be produced by processes analogous to the Process Variants (a) and (b).

In all the Process Variants, any inert organic solvent may be used as diluent. Preferred solvents include hydrocarbons (such as benzine or benzene), halogenated hydrocarbons (such as chloroform or chlorobenzene) and ethers (such as diethyl ether or dioxane). The use of added diluents is, however, not always necessary, because it is also possible to use one of the reactants itself as the diluent and to employ it in a large excess.

In Process Variants (b) and (c), alcohols (such as ethanol), acid amides (such as dimethylformamide), sulphoxides (such as dimethyl sulphoxide) and sulphones (such as tetramethylenesulphone) can be used as diluents either individually or as mixtures, as well as those mentioned above.

Any of the customary acid-binding agents can be employed. Preferred acid-binding agents include alkali metal and alkaline earth metal carbonates and bicarbonates, tertiary amines (such as pyridine or triethylamine), and secondary amines (such as dicyclohexylamine).

The reaction temperatures can be varied over a substantial range. In general, the reactions in all the Process Variants are carried out at temperatures between $-10°C$ and $+180°C$. preferably between $10°$ to $130°C$. The reactions can be carried out either under atmospheric pressure or elevated pressure. In general, atmospheric pressure is preferred.

In carrying out the process according to the invention, 1 mol of the benzomorphan is as a rule reacted with 1 to 5 mols of the second reactant.

The benzomorphanes of the present invention and their pharmaceutically acceptable nontoxic salts can be interconverted according to techniques per se known.

The pharmaceutical compositions of the present invention contain a major or minor amount e.g. 0.1 to 99.5%, preferably 0.5 to 90%, of benzomorphan as above defined in combination with a pharmaceutically acceptable nontoxic inert diluent or carrier, the carrier comprising one or more solid, semi-solid or liquid diluent, filler and formation adjuvant which is nontoxic, inert and pharmaceutically acceptable. Such pharmaceutical compositions are preferably in dosage unit form; i.e., physically discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single does. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of aministration and the nature and gravity of the illness, generally the dosage for intravenous administration will be from 0.1 to 200, and preferably 1 to 100, mg/kg of body weight per day, whereas the oral dosage will be 1 to 200 mg/kg of body weight per day. In some instances a sufficient thereapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl, cellulose, an alginate, gelatin, or polyvinyl pyrrolidone, a solution retardant such as paraffin, a resorption accelerator such as a quaternary salt and-/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinuish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, supensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons.

The preferred daily dose for intravenous administration is 5 mg to 20 g, preferably 50 mg to 10.0 g of active agent; for oral administration, 50 mg to 20 g is the preferred daily dose.

While the routes of administration include oral and parenteral (i.e., intramuscular, intraperitoneal, and intravenous), oral and intravenous administration are particularly preferred.

The preferred pharmaceutical compositions are therefore those in a form suitable for oral administration such as tablets and suspensions and those suitable for intravenous administration such as solutions and suspensions.

The Table which follows lists the toxicity in rats, the analgesic action in rats, the therapeutic index (which can be calculated from both) and the morphine-replacing action or morphine-antagonistic action of some compounds according to the invention, by way of examples. The numbering of the compounds is the same as the numbering of the preparative examples. The comparison compounds were used in the form of their salts - morphine as the hydrochloride trihydrate, codeine as the phosphate, and pethidine and pentazocine as the hydrochlorides. The ED50 and LD50 were calculated relative to the base.

The analgesic action was determined by means of the heat radiation test on rat tails (method: H. G. Wolff et al., J.Clin. Invest. 19, 659 – 680 (1940) and the morphine- agonistic (replacement action) and antagonistic actions of the substances were examined on morphine-dependent monkeys (methods: G. A. Deneau, Dissertation Univ. of Michigan 1956; M. H. Seevers, J.Pharm..exper. Ther. 56, 147 – 156 (1936)) and on morphine-dependent rats (methods: W. R. Buckett, Psychopharmacologia 6, 410 (1964)); W. R. Martin et al., Psychopharmacologia 4, 247–260 (1963)).

TABLE

| Substance | Toxicity in rats, LD 50, mg/kg, s.c. | Analgesic action in heat radiation test on rat tails, ED 50, mg/kg, s.c. | Therapeutic index $\frac{LD\ 50}{ED\ 50}$ |
| --- | --- | --- | --- |
| Morphine | 122 (76–217) | 1.78 (0.77–2.64) | 69 |
| Codeine | 202 (97–352) | 4.5 (3.6–5.9) | 51 |
| Pethidine | 113 (84–136) | 5.7 (3.7–7.3) | 20 |
| Pentazocine | 140 (107–190) | 4.8 (3.5–6.7) | 29 |
| 1 | 352 (182–964) | 0.42 (0.22–0.63) | 838 |
| 2a | 296 (168–566) | 0.49 (0.26–0.68) | 604 |
| 2b | ~300 | 1.0 (0.67–1.5) | ~300 |
| 4a | >500 | 0.97 (0.69–1.4) | >515 |
| 4d | — | 0.35 (0.18–0.54) | — |
| 4e | — | 0.42 (0.22–0.63) | — |
| 6a | — | 0.42 (0.22–0.61) | — |

| Substance | Morphine-dependent monkeys | | Morphine-dependent rats | |
| --- | --- | --- | --- | --- |
| | Morphine-replacement action (elimination of withdrawal symptoms) | Morphine-antagonistic action (provocation of withdrawal symptoms) | Morphine replacement action (elimination of withdrawal symptoms) | Morphine-antagonistic action (provocation of withdrawal symptoms) |
| Morphine | — | — | — | — |
| Codeine | 3 | — | 3 | 0 |
| Pethidine | — | — | — | — |
| Pentazocine | — | 2 | 1 | 2 |
| 1 | 0 | 1–2 | 0 | 2 |
| 2a | 0 | 2 | 0 | 2 |
| 2b | — | — | 0 | 1 |
| 4a | — | — | 0 | 1 |
| 4d | — | 3 | 0 | 2 |
| 4e | — | 2 | — | — |
| 6a | — | 3 | — | — |

| Substance | Toxicity in rats, LD 50, mg/kg, s.c. | Analgesic action in heat radiation test on rat tails, ED 50, mg/kg, s.c. | Therapeutic index $\frac{LD\ 50}{ED\ 50}$ |
| --- | --- | --- | --- |

TABLE-continued

| Substance | Toxicity in rats, LD 50, mg/kg, s.c. | Analgesic action in heat radiation test on rat tails, ED 50, mg/kg, s.c. | Therapeutic index $\frac{LD\ 50}{ED\ 50}$ |
|---|---|---|---|
| 6b  | —    | 0.31 (0.19–0.47) | —      |
| 7   | ~400 | 1.6  (0.96–3.0)  | ~258   |
| 8   | ~425 | 1.6  (0.83–2.6)  | ~262   |
| 9   | >500 | 0.61 (0.43–0.95) | >820   |
| 10a | >500 | 0.62 (0.32–1.3)  | >806   |
| 10b | >500 | 0.42 (0.22–0.63) | >1,190 |
| 11  | —    | 0.47 (0.24–0.88) | —      |
| 17  | —    | 0.96 (0.37–1.89) | —      |
| 18  | —    | 1.36 (0.80–2.16) | —      |
| 20  | —    | 1.2  (0.67–2.02) | —      |
| 21a | —    | 1.2  (0.62–2.23) | —      |
| 23  | —    | 1.2  (0.62–2.23) | —      |

| Substance | Morphine-dependent monkeys | | Morphine-dependent rats | |
|---|---|---|---|---|
| | Morphine-replacement action (elimination of withdrawal symptoms) | Morphine-antagonistic action (provocation of withdrawal symptoms) | Morphine-replacement action (elimination of withdrawal symptoms) | Morphine-antagonistic action (provocation of withdrawal symptoms) |
| 6b  | — | 3 | —   | — |
| 7   | — | — | 0   | — |
| 8   | — | — | 1   | 1 |
| 9   | — | — | 0–1 | 1 |
| 10a | — | — | 0   | 2 |
| 10b | — | — | 0   | 1 |
| 11  | — | 1 | —   | — |
| 17  | — | 2 | —   | — |
| 18  | — | 2 | —   | — |
| 20  | — | 1 | —   | — |
| 21a | — | 2 | —   | — |
| 23  | — | 2 | —   | — |

The following non-limitative examples more particularly illustrate the present invention:

EXAMPLE 1

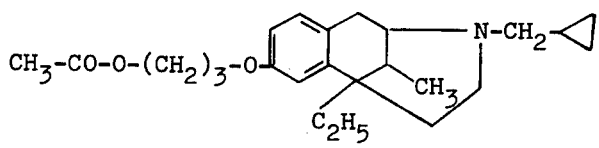

6.9g of 2-cyclopropylmethyl-5-ethyl-9-methyl-2'-[3-hydroxypropoxy-(1)]-6,7-benzomorphan, produced according to Belgian Patent 750,486 (Bayer AG), Example 8, boiling point 210°–230°C/0.01 mm Hg, are stirred with 11 ccs of acetic anhydride overnight at room temperature, and then for 1 hour at 100°C. After cooling, the mixture is poured into ice water, rendered strongly alkaline with concentrated potassium hydroxide solution and immediately extracted 5 times with ether. The combined extracts are washed once with water, dried over sodium sulphate and evaporated. 2-Cyclopropylmethyl-5-ethyl-9-methyl-2'-[3-acetoxypropoxy-(1)]-6,7-benzomorphan boils at 210°–215°C/0.01 mm Hg. The yield is 6.4g.

Hydrochloride, melting point 108–110°C; neutral naphthalene-1,5-disulphonate, melting point 160°–164°C.

EXAMPLE 2

The following can be produced as described in Example 1:

a. 2-Cyclopropylmethyl-5-ethyl-9-methyl-2'-[3-propionyloxy-propoxy-(1)]-6,7-benzomorphan, boiling point 200°–220°C/0.01 mm Hg.

From: the reacting benzomorphan of Example 1 and propionic acid anhydride.

b. 2-Cyclopropylmethyl-5-ethyl-9-methyl-2'-[3-isobutyryloxy-propoxy-(1)]-6,7-benzomorphan, boiling point 230°–240°C/0.01 mm Hg. From: the reacting bemzomorphan of Example 1 and isobutyric acid anhydride.

EXAMPLE 3: :

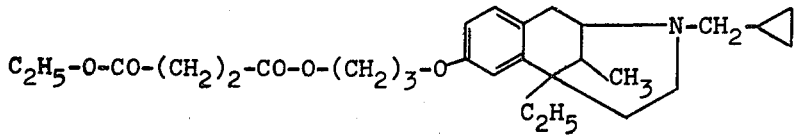

10.3g of 2-cyclopropylmethyl-5-ethyl-9-methyl-2'-[3-hydroxypropoxy-(1)]-6,7-benzomorphan, boiling point 210°–230°C/0.01 mm Hg, are dissolved in 30 ccs of absolute benzene and 10 ccs of absolute pyridine. 12.3g of succinic acid half-ester chloride are added dropwise and the mixture is stirred for 2 hours at room temperature and 10 hours under reflux. After cooling, it is diluted with ether and the mixture is well shaken with dilute sodium hydroxide solution, washed with water, dried over sodium sulphate and distilled. 2-Cyclopropylmethyl-5-ethyl-9-methyl-2'-[3-($\beta$-ethoxycarbonyl-propionyloxy)-propoxy-(1)]-6,7-benzomorphan boils at 190°–200°C/0.001 mm Hg.

The yield is 6.3g.

EXAMPLE 4

The following can be produced as described in Example 3:

a. 2-Cyclopropylmethyl-5-ethyl-9-methyl-2'-[3-pivaloyloxy-propoxy-(1)]-6,7-benzomorphan, boiling point 220°–234°C/0.01 mm Hg.

From: the reaction benzomorphan of Example 3 and pivalic acid chloride.

b. 2-Cyclopropylmethyl-5-ethyl-9-methyl-2'-[3-dodecanoyloxy-propoxy-(1)]-6,7-benzomorphan, boiling point 210°–230°C/0.01 mm Hg.

From: the reacting benzomorphan of Example 3 and dodecanic acid chloride.

c. 2-Cyclopropylmethyl-5-ethyl-9-methyl-2'-[3-ethoxyacetoxy-propoxy-(1)]-6,7-benzomorphan, boiling point 210°–230°C/0.005 mm Hg. From: the reacting benzomorphan of Example 3 and ethoxyacetic acid chloride.

d. 2-Cyclopropylmethyl-5-ethyl-9-methyl-2'-[3-crotonoyloxy-propoxy-(1)]-6,7-benzomorphan, boiling point 202°–208°C/0.01 mm Hg. Neutral naphthalene-1,5-disulphonate, melting point 163°–164°C. From: the reacting benzomorphan of Example 3 and crotonic acid chloride.

e. 2-Cyclopropylmethyl-5-ethyl-9-methyl-2'-[3-benzoyloxy-propoxy-(1)]-6,7-benzomorphan, boiling point 228°–234°C/0.02 mm Hg. From: the reacting benzomorphan of Example 3 and benzoic acid chloride.

EXAMPLE 5

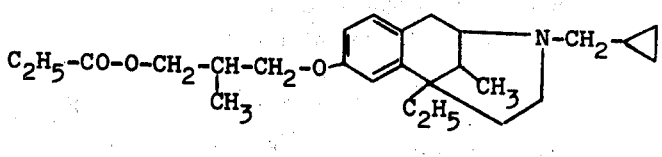

8.8g of 2-cyclopropylmethyl-5-ethyl-9-methyl-2'-[3-hydroxyisobutoxy-(1)]-6,7-benzomorphan, produced as described for the 3-hydroxypropoxy compound in Belgian Pat. No. 750,486 (Bayer AG), Example 8, and 15.8g of propionic anhydride, are heated for 15 hours to 110°–120°C and the mixture is subsequently distilled. 2-Cyclopropylmethyl-5-ethyl-9-methyl-2'-[3-propionyloxy-isobutoxy-(1)]-6,7-benzomorphan boils at 208°–212°C/0.02 mm Hg and the yield is 7.8g. Neutral naphthalene-1,5-disulphonate, melting point 127°C.

EXAMPLE 6

The following can be produced as described in Example 5:

a. 2-Cyclopropylmethyl-5-ethyl-9-methyl-2'-[3-acetoxyisobutoxy-(1)]-6,7-benzomorphan, boiling point 198°–202°C/0.01 mm Hg. From: the reacting benzomorphan of Example 5 and acetic acid anhydride.

b. 2-Cyclopropylmethyl-5-ethyl-9-methyl-2'-[3-crotonoyloxyisobutoxy-(1)]-6,7-benzomorphan, boiling point 210°–212°C/0.01 mm Hg. From: the reacting benzomorphan of Example 5 and crotonic acid anhydride.

EXAMPLE 7

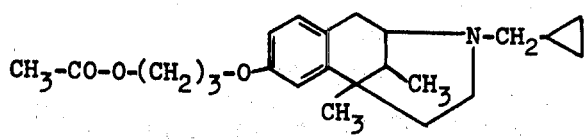

9.9g of 2-cyclopropylmethyl-5-9-dimethyl-2'-[3-hydroxypropoxy-(1)]-6,7-benzomorphan, produced according to Belgian Pat. 750,486 (Bayer AG), Example 8, analogously to the 5-ethyl compound (boiling point 210°–216°C/0.01 mm Hg) are reacted with 17 ccs of acetic anhydride analogously to Example 1.

2-Cyclopropylmethyl-5,9-dimethyl-2'-[3-acetoxy-propoxy-(1)]-6,7-benzomorphan boils at 176°–192°/0.005 mm Hg and the yield is 9.2g.

EXAMPLE 8

The following can be produced as described in Example 7:

2-Cyclopropylmethyl-5-9-dimethyl-2'-[3-propionyloxypropoxy-(1)]-6,7-benzomorphan, boiling point 200°–220°C/0.01 mm Hg. From: the reacting benzomorphan of Example 7 and propionic acid anhydride

EXAMPLE 9

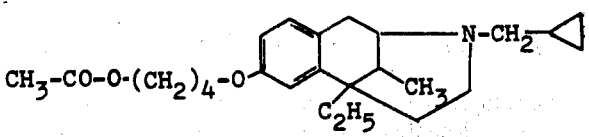

10.7g of 2-cyclopropylmethyl-5-ethyl-9-methyl-2'-[4-hydroxybutoxy-(1)]-6,7-benzomorphan, produced according to Belgian Patent 750,486 (Bayer AG), Example 17, boiling point 210°–226°C/0.01 mm Hg., are reacted with 17 ccs of acetic anhydride as described in Example 1. 2-Cyclopropylmethyl-5-ethyl-9-methyl-2'-[4-acetoxybutoxy-(1)]-6,7-benzomorphan boils at 210°–230°C/0.01 mm Hg and the yield is 9.0g.

EXAMPLE 10

The following can be produced as described in Example 9:

a. 2-Cyclopropylmethyl-5-ethyl-9-methyl-2'-[4-propionyloxypropoxy-(1)]-6,7-benzomorphan, boiling point 240°–246°C/0.01 mm Hg.

From: the reacting benzomorphan of Example 9 and propionic acid anhydride.

b. 2-Cyclopropylmethyl-5-ethyl-9-methyl-2'-[4-isobutyryloxybutoxy-(1)]-6,7-benzomorphan, boiling point 200°–215°C/0.005 mm Hg. From: the reacting benzomorphan of Example 9 and isobutylic acid anhydride c. 2-Cyclopropylmethyl-5-ethyl-9-methyl-2'-[4-undecen-(10)-oyloxybutoxy-(1)]-6,7-benzomorphan, boiling point 190°–220°C/0.001 mm Hg. From: the reacting benzomorphan of Example 9 and undecen acid chloride.

EXAMPLE 11

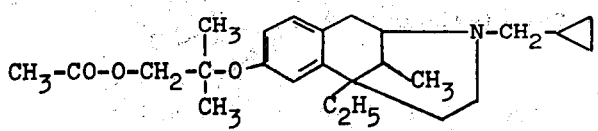

10.7g of 2-cyclopropylmethyl-5-ethyl-9-methyl-2'-[1-hydroxy-2-methyl-propoxy-(2)]-6,7-benzomorphan, boiling point 190°–200°C/0.01 mm Hg., produced by reduction of 2-cyclopropylcarbonyl-5-ethyl-9-methyl-2'-[1-cyclopropylcarbonyloxy-2-methyl-propoxy-(2)]-6,7-benzomorphan with lithium aluminium hydride in tetrahydrofurane, are reacted with 17 ccs of aceti anhydride as described in Example 1. 2-Cyclopropylmethyl-5-ethyl-9-methyl-[1-acetoxy-2-methyl-propoxy-(2)]-6,7-benzomorphan boils at 209° to 223°C/0.01 mm Hg and the yield is 4.9g.

EXAMPLE 12

The following can be produced as described in Example 11:
2-Cyclopropylmethyl-5-methyl-9-methyl-2'-[1-propionyloxy-2-methylpropoxy-(2)]-6,7-benzomorphan, boiling point 194°–198°C/0.01 mm Hg. From: the reacting benzomorphan of Example 11 and propionic acid anhydride

EXAMPLE 13

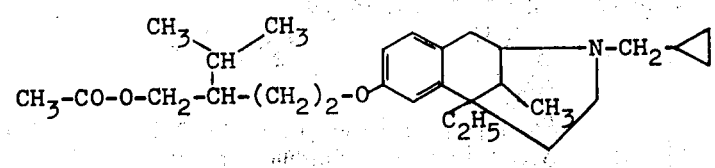

11.1g of 2-cyclopropylmethyl-5-ethyl-9-methyl-2'-[5-hydroxypentoxy-(1)]-6,7-benzomorphan, boiling point 211°–222°C/0.01 mm Hg, produced by reduction of 2-cyclopropylcarbonyl-5-ethyl-9-methyl-2'-[4-ethoxycarbonylbutoxy-(1)]-6,7-benzomorphan with lithium aluminium hydride in tetrahydrofuran, are reacted with 17 ccs of acetic anhydride as described in Example 1. 2-Cyclopropylmethyl-5-ethyl-9-methyl-2'-[5-acetoxypentoxy-(1)]-6,7-benzomorphan boils at 210°–220°C/0.01 mm Hg and the yield is 10.0g.

EXAMPLE 14

The following can be produced as described in Example 13:
2-Cyclopropylmethyl-5-ethyl-9-methyl-2'-[5-propionyloxypentoxy-(1)]-6,7-benzomorphan, boiling point 214°–220°C/0.01 mm Hg.
From: the reacting benzomorphan of Example 13 and propionic acid anhydride.

EXAMPLE 15:

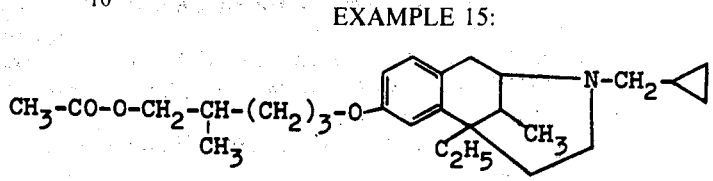

11.6g of 2-cyclopropylmethyl-5-ethyl-9-methyl-2'-[5-hydroxy-4-methylpentoxy-(1)]-6,7-benzomorphan, boiling point 230°–240°C/0.01 mm Hg., produced by reduction of 2-cyclopropylcarbonyl-5-ethyl-9-methyl-2'-[4-ethoxycarbonylpentoxy-(1)]-6,7-benzomorphan with lithium aluminium hydride in tetrahydrofuran, are reacted with 17 ccs of acetic anhydride as described in Example 1. 2-Cyclopropylmethyl-5-ethyl-9-methyl-2'-[5-acetoxy-4-methylpentoxy-(1)]-6,7-benzomorphan boils at 258°–262°C/2 mm Hg and the yield is 10.6g.

EXAMPLE 16

The following can be produced as described in Example 15:
2-Cyclopropylmethyl-5-ethyl-9-methyl-2'-[5-propionyloxy-4-methylpentoxy-(1)]-6,7-benzomorphan, boiling point 240°–245°C/0.02 mm Hg.
From: the reacting benzomorphan of Example 15 and propionic acid anhydride.

EXAMPLE 17

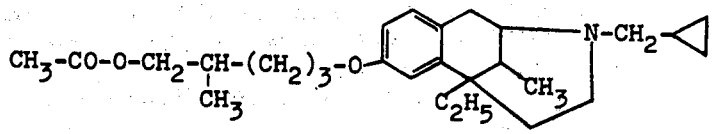

11.2g of 2-cyclopropylmethyl-5-ethyl-9-methyl-2'-[4-hydroxy-2-methylbutoxy-(1)]-6,7-benzomorphan, boiling point 200°–230°C/0.01 mm Hg, produced by reduction of 2-cyclopropylcarbonyl-5-ethyl-9-methyl-2'-[3-butoxycarbonyl-2-methylpropoxy-(1)]-6,7-benzomorphan with lithium aluminium hydride in tetrahydrofuran are reacted with 17 ccs of acetic anhydride as described in Example 1. 2-Cyclopropylmethyl-5-ethyl-9-methyl-2'-[4-acetoxy-2-methylbutoxy-(1)]-6,7-benzomorphan boils at 210°–240°C/0.5 mm Hg and the yield is 8.0g.

EXAMPLE 18

The following can be produced as described in Example 17:
2-Cyclopropylmethyl-5-ethyl-9-methyl-2'-[4-propionyloxy-2-methylbutoxy-(1)-6,7-benzomorphan, boiling point 200°–240°C/0.01 mm Hg.
From: the reacting benzomorphan of Example 17 and propionic acid anhydride.

EXAMPLE 19

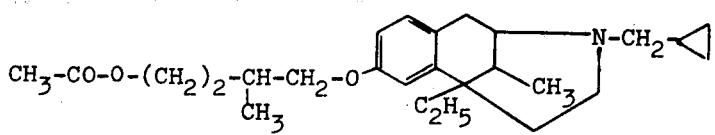

12.0g of 2-cyclopropylmethyl-5-ethyl-9-methyl-2'-[4-hydroxy-3-isopropylbutoxy-(1)]-6,7-benzomorphan, boiling point 200°–230°C/0.01 mm Hg., produced by reduction of 2-cyclopropylcarbonyl-5-ethyl-9-methyl-2'-[3-butoxycarbonyl-4-methylpentoxy-(1)]-6,7-benzomorphan with lithium aluminium hydride in tetrahydrofurane, are reacted with 17 ccs of acetic anhydride as described in Example 1. 2-Cyclopropylmethyl-5-ethyl-9-methyl-2'-[4-acetoxy-3-isopropylbutoxy-(1)]-6,7-benzomorphan boils at 200°–220°C/0.01 mm Hg and the yield is 9.2g.

EXAMPLE 20

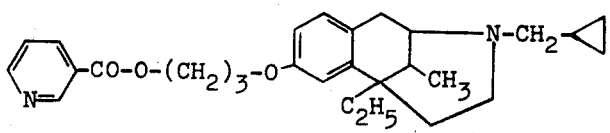

A solution of 3.2g of nicotinic acid chloride in benzene is rapidly added dropwise to a solution of 5.5g of 2-cyclopropylmethyl-5-ethyl-9-methyl-2'-[3-hydroxypropoxy-(1)]-6,7-benzomorphan and 3.8g of dimethylaniline in 70 ccs of absolute benzene, after which a distinct exothermic reaction is observed. The mixture is stirred for 15 hours at 50°C, cooled and washed with water and diluted sodium hydroxide solution, the organic phase is dried over sodium sulphate and evaporated in vacuo, and the residue is distilled. 4.2g of 2-cyclopropylmethyl-5-ethyl-9-methyl-2'-[3-nicotinoyloxypropoxy-(1)-6,7-benzomorphan of boiling point 258°–260°C/0.05 mm Hg. are obtained.

EXAMPLE 21

The following can be produced as described in Example 20:

a. 2-Cyclopropylmethyl-5-ethyl-9-methyl-2'-[3-phenoxyacetoxypropoxy-(1)]-6,7-benzomorphan, boiling point 250°–252°C/0.05 mm Hg. From: the reacting benzomorphan of Example 20 and phenoxy acetic acid chloride.

b. 2-Cyclopropylmethyl-5-ethyl-9-methyl-2'-[3-ethoxycarboxypropoxy-(1)]-6,7-benzomorphan, boiling point 214°–219°C/0.05 mm Hg. From: the reacting benzomorphan of Example 20 and chloroformic acid ethylester

EXAMPLE 22

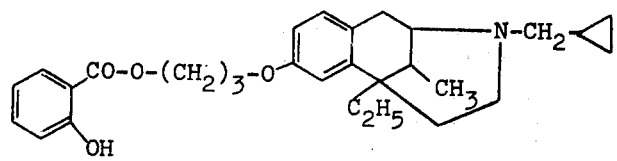

Hydrogen bromide is passed into a solution of 5.4g of 2-cyclopropylmethyl-5-ethyl-9-methyl-2'-[3-hydroxypropoxy-(1)]-6,7-benzomorphan in 50 ccs of dry chloroform, while cooling with ice, until the mixture reacts acid to Congo Red. A solution of 6.8g of freshly distilled thionyl bromide in dry chloroform is then added dropwise and the mixture is stirred for a further hour under reflux and then evaporated to dryness in vacuo, the residue is taken up in fresh chloroform, this solution is evaporated to dryness in vacuo, and this operation is repeated several times. Finally, the evaporation residue is taken up in 50 ccs of dry dimethylformamide and this solution is added dropwise to a solution, prewarmed to 70°–80°C of 6.1g of dicyclohexylamine and 2.2g of salicylic acid in 70 ccs of dry dimethylformamide. The mixture is stirred for a further 2 hours at this temperature, the dicyclohexylamine hydrobromide is filtered off and the filtrate is evaporated to dryness in vacuo. The residue is digested with a little ether, which is discarded. Thereafter the product which remains is partitioned between ether and ice-cold N/5 sodium hydroxide solution and the alkaline solution is purified by extraction with ether. The aqueous phase is neutralized with acetic acid and extracted with ether-methylene chloride (2:1). The extracts are dried over sodium sulphate and evaporated. The residue consists of 2-cyclopropylmethyl-5-ethyl-9-methyl-2'-[3-salicyloyloxypropoxy-(1)]-6,7-benzomorphan.

EXAMPLE 23

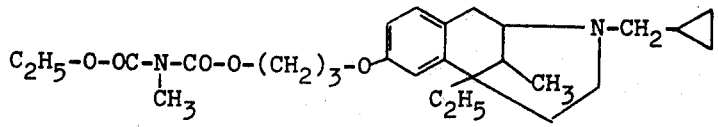

A solution of 2.9g of N-ethoxycarbonyl-N-methylcarbamic acid chloride produced as described in German Patent Specification No. 1,259,871) is rapidly added dropwise to a solution of 5.4g of 2-cyclopropylmethyl-5-ethyl-9-methyl-2'-[3-hydroxypropoxy-(1)]-6,7-benzomorphan and 2.2g of dimethylaniline in 70 ccs of absolute benzene. After the exothermic reaction has subsided, the mixture is stirred for 15 hours at 50°C and cooled and the organic phase is washed with sodium carbonate solution and water and then subjected to a steam distillation. The resinous residue in the flask is extracted with ether and the ether solution is dried over sodium sulphate and evaporated in vacuo until the residue is free of ether. 3.2g of 2-cyclopropylmethyl-5-ethyl-9-methyl-2'-[3-N-ethoxycarbonyl-N-methyl-carbamoyloxypropoxy-(1)]-6,7-benzomorphan are thus obtained.

EXAMPLE 24

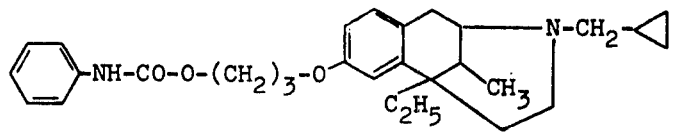

3.9g of phenylisocyanate in 20 ccs of absolute benzene are added to 10.3g of 2-cyclopropylmethyl-5-ethyl-9-methyl-2'-[3-hydroxypropoxy-(1)]-6,7-benzomorphan in 30 ccs of absolute benzene at room temperature. The mixture is stirred for 3 hours at room temperature and 3 hours under reflux and is evaporated in vacuo, the residue is taken up in acetone, and a solution of 4.32g of naphthalene-1,5-disulphonic acid in acetone is added, followed by absolute ether. The precipitate is filtered off (melting point 133°C, with decomposition) and is partitioned between dilute sodium hydroxide solution and ether. The aqueous phase is additionally extracted 3 times with ether and the combined ether phases are washed once with water, dried over sodium sulphate and evaporated in vacuo. The oily residue (10.0g) consists of 2-cyclopropylmethyl-5-ethyl-9-methyl-2'-[3-anilinocarboxypropoxy-(1)]-6,7-benzomorphan.

EXAMPLE 25

The following can be produced as described in Example 24:

2-Cyclopropylmethyl-5-ethyl-9-methyl-2'-[3-ethylaminocarboxypropoxy-(1)]-6,7-benzomorphan, boiling point 220°–227°C/0.01 mm Hg. From: the reacting benzomorphan of Example 24 and ethylisocyanate

EXAMPLE 26

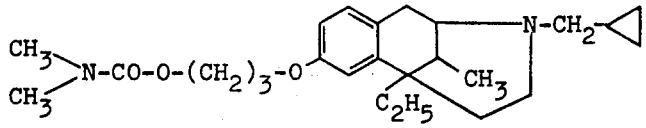

10.3g of 2-cyclopropylmethyl-5-ethyl-9-methyl-2'-[3-hydroxypropoxy-(1)]-6,7-benzomorphan are dissolved in 35 ccs of absolute benzene and 10 ccs of dry pyridine and 3.6g of dimethylcarbamic acid chloride in 10 ccs of absolute benzene are added. The mixture is stirred for a further 8 hours under reflux and is evaporated to dryness in vacuo, the residue is taken up in water and rendered alkaline with concentrated sodium hydroxide solution, and the mixture is extracted 5 times with ether-methylene chloride (2:1). The combined extracts are washed with water, dried over sodium sulphate and evaporated in vacuo. 2-Cyclopropylmethyl-5-ethyl-9-methyl-2'-[3-dimethylaminocarboxypropoxy-(1)-6,7-benzomorphan boils at 225°–232°C/0.01 mm Hg. The yield is 7.2g.

EXAMPLE 27

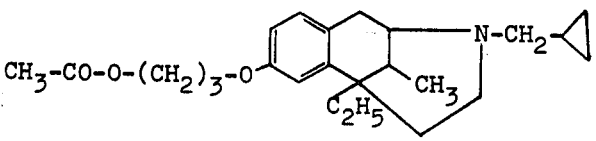

28.5g of 2-cyclopropylmethyl-5-ethyl-9-methyl-2'-hydroxy-6,7-benzomorphan are suspended in 170 ccs of absolute methanol and a solution of 2.4g of sodium in absolute methanol is added. The mixture is stirred for 15 hours under reflux and is evaporated to dryness in vacuo and the residue is mixed with 230 ccs of dry dimethylformamide of which about 30 ccs are distilled off in vacuo. Thereafter 18.2g of acetic acid γ-bromopropyl ester are slowly added at room temperature and the mixture is stirred for 2 hours at room temperature and a further 18 hours at 60°C. Thereafter it is evaporated to dryness in vacuo, the residue is taken up in ice water and the mixture is rendered alkaline with concentrated sodium hydroxide solution and immediately extracted 5 times with ether-methylene chloride (2:1). The combined extracts are washed once with water, dried over sodium sulphate and evaporated to dryness in vacuo, and the residue is distilled. 2-Cyclopropylmethyl-5-ethyl-9-methyl-2'-[3-acetoxypropoxy-(1)]-6,7-benzomorphan boils at 210°–220°C/0.01 mm Hg. The yield is 34.3g.

EXAMPLE 28

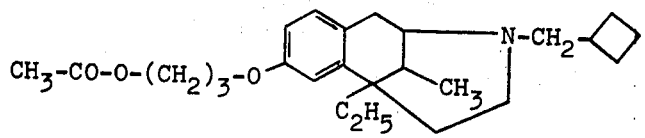

10.8g of 2-cyclobutylmethyl-5-ethyl-9-methyl-2'-[3-hydroxy-propoxy-(1)]-6,7-benzomorphan, boiling point 220°–240°C/0.01 mm Hg, produced by reduction of 2-cyclobutylcarbonyl-5-ethyl-9-methyl-2'-[3-cyclobutylcarbonyloxypropoxy-(1)]-6,7-benzomorphane with lithium aluminium hydride in tetrahydrofuran, are stirred with 17 ccs of acetic anhydride overnight at room temperature and for 1 hour at 100°C. After cooling, the mixture is poured into ice water, rendered strongly alkaline with concentrated potassium hydroxide solution and immediately extracted 5 times with ether. The combined extracts are washed once with water, dried over sodium sulphate and evaporated. After distillation, 6.3g of 2-cyclobutylmethyl-5-ethyl-9-methyl-2'-[3-acetoxypropoxy-(1)]-6,7-benzomorphan of boiling point 190°–198°C/0.01 mm Hg are obtained.

EXAMPLE 29

The following can be produced as described in Example 28: 2-Cyclobutylmethyl-5-ethyl-9-methyl-2'-[3-propionyloxypropoxy-(1)]-6,7-benzomorphan, boiling point 200°–220°C/0.01 mm Hg. From: the reacting benzomorphan of Example 28 and propionic acid anhydride.

EXAMPLE 30

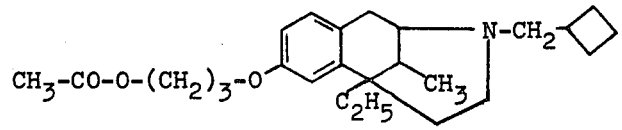

21 a. 23.1g of 5-ethyl-9-methyl-2'-hydroxy-6,7-benzomorphan are added to a suspension of 16.5g of finely powdered potassium carbonate in 200 ccs of dry acetone and the mixture is stirred for one-half hour under reflux. Thereafter 18.2g of acetic acid γ-bromopropyl ester are added dropwise over the course of 1 hour at room temperature and the mixture is stirred first for 3 hours at room temperature and then overnight under reflux. After cooling, the mixture is filtered, the filtrate is evaporated to dryness and the residue is distilled in vacuo. 5-Ethyl-9-methyl-2'-[3-acetoxypropoxy-(1)]-6,7-benzomorphan boils at 230°–235°C/0.05 mm Hg. The yield is 16.1g.

b. The above compound is dissolved in 50 ccs of dry acetone and 4.5g of sodium bicarbonate and 4.8g of cyclobutylmethyl chloride are added. The mixture is stirred overnight under reflux and evaporated to dryness in vacuo, the residue is taken up in ice water, a few ccs of concentrated sodium hydroxide solution are added, this mixture is extracted 5 times with ether and the combined extracts are washed once with water, dried over sodium sulphate and evaporated to dryness in vacuo. The resulting 2-cyclobutylmethyl-5-ethyl-9-methyl-2'-[3-acetoxypropoxy-(1)]-6,7-benzomorphan is purified by vacuum distillation and is identical with the product produced as described in Example 28.

What is claimed:

1. A benzomorphan of the formula

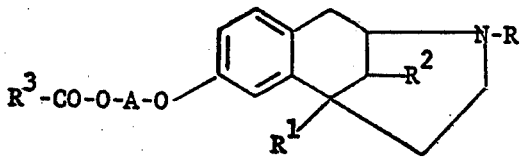

or a pharmaceutically acceptable nontoxic salt thereof wherein

R is cyclopropylmethyl or cyclobutylmethyl;

$R^1$ and $R^2$ are the same or different and each is lower alkyl; and $R^3$ is straight- or branched-chain alkyl of 1 to 6 carbon atoms, straight- or branched-chain alkenyl of 2 to 6 carbon atoms or cycloalkyl of 3 to 6 carbon atoms unsubstituted or substituted by alkoxy of 1 to 4 carbon atoms, alkoxycarbonyl of 1 to 4 carbon atoms in the alkoxy moiety, phenoxy, alkoxycarbonylamino of 1 to 4 carbon atoms in the alkoxy moiety or alkoxycarbonyl-alkylamino of 1 or 2 carbon atoms in the alkoxy moiety and 1 or 2 carbon atoms in the alkyl moiety; phenyl or pyridyl unsubstituted or substituted by hydroxy, alkyl of 1 or 2 carbon atoms, alkoxy of 1 or 2 carbon atoms or alkylamino of 1 or 2 carbon atoms; alkylamino of 1 or 2 carbon atoms, dialkylamino of 1 or 2 carbon atoms in each alkyl moiety; phenylamino; alkoxy of 1 or 2 carbon atoms; alkoxycarbonyl-alkylamino of 1 or 2 carbon atoms in the alkoxy moiety; or alkoxycarbonyl-alkylamino of 1 or 2 carbon atoms in the alkoxy moiety and 1 or 2 carbon atoms in the alkyl moiety; and A is alkylene or alkylidene of 2 to 7 carbon atoms.

2. A compound according to claim 1 wherein $R^1$ and $R^2$ are the same or different and each is methyl or ethyl.

3. A compound according to claim 1 wherein $R^1$ and $R^2$ are the same or different and each is methyl or ethyl;

22

$R^3$ is straight- or branched-chain alkyl of 1 to 11 carbon atoms; straight- or branched-chain alkenyl of 2 to 6 carbon atoms; phenyl; salicyl; nicotinyl; alkylamino of 1 or 2 carbon atoms; dialkylamino of 1 or 2 carbon atoms; phenylamino; alkoxy of 1 or 2 carbon atoms or alkoxycarbonylalkylamino of 1 or 2 carbon atoms in the alkoxy moiety and 1 or 2 carbon atoms in the alkyl moiety; and A is alkylene or alkylidene of 3 to 7 carbon atoms.

4. A compound according to claim 1 wherein $R^1$ is methyl or ethyl;

$R^2$ is methyl;

$R^3$ is methyl; ethyl; propyl; butyl; undecyl; ethoxymethyl; ethoxycarbonylethyl; allyl; decenyl; phenyl; salicyl; phenoxymethyl; phenylamino; nicotinyl; ethoxy; ethylamino; dimethylamino; or ethoxycarbonylmethylamide; and A is propylene; butylene; pentylene; methylpropylene, dimethylethylene; methylbutylene; methylpentylene; or isopropylbutylene.

5. A salt of a compound of claim 1 wherein the salt is selected from the group consisting of the hydrochloride, the sulphate, the phosphate, the tartrate, the citrate, and the naphthalene-1,5-disulphonate.

6. A salt according to claim 5 wherein the salt is the hydrochloride or the naphthalene-1,5-disulphonate.

7. The compound according to claim 1 which is 2-cyclopropylmethyl-5-ethyl-9-methyl-2'-[3-acetoxypropoxy-(1)]-6,7-benzomorphan or the hydrochloride or naphthalene-1,5-disulphonate thereof.

8. The compound according to claim 1 which is 2-cyclopropylmethyl-5-ethyl-9-methyl-2'-[3-propionyloxypropoxy-(1)]-6,7-benzomorphan.

9. The compound according to claim 1 which is 2-cyclopropylmethyl-5-ethyl-9-methyl-2'-[3-isobutyryloxypropoxy-(1)]-6,7-benzomorphan.

10. The compound according to claim 1 which is 2-cyclopropylmethyl-5-ethyl-9-methyl-2'-[3-pivaloyloxypropoxy-(1)]-6,7-benzomorphan.

11. The compound according to claim 1 which is 2-cyclopropylmethyl-5-ethyl-9-methyl-2'-[3-crotonyloxypropoxy-(1)]-6,7-benzomorphan.

12. The compound according to claim 1 which is 2-cyclopropylmethyl-5-ethyl-9-methyl-2'-[3-benzoyloxypropoxy-(1)]-6,7-benzomorphan.

13. The compound according to claim 1 which is 2-cyclopropylmethyl-5-ethyl-9-methyl-2'-[3-acetoxyisobutoxy-(1)]-6,7-benzomorphan.

14. The compound according to claim 1 which is 2-cyclopropylmethyl-5-ethyl-9-methyl-2'-[3-crotonyloxyisobutoxy-(1)]-6,7-benzomorphan.

15. The compound according to claim 1 which is 2-cyclopropylmethyl-5,9-dimethyl-2'-[3-acetoxypropoxy-(1)]-6,7-benzomorphan.

16. The compound according to claim 1 which is 2-cyclopropylmethyl-5,9-dimethyl-2'-[3-propionyloxypropoxy-(1)]-6,7-benzomorphan.

17. The compound according to claim 1 which is 2-cyclopropylmethyl-5-ethyl-9-methyl-2'-[4-acetoxybutoxy-(1)]-6,7-benzomorphan.

18. The compound according to claim 1 which is 2-cyclopropylmethyl-5-ethyl-9-methyl-2'-[4-propionyloxypropoxy-(1)]-6,7-benzomorphan.

19. The compound according to claim 1 which is 2-cyclopropylmethyl-5-ethyl-9-methyl-2'-[4-isobutyryloxybutoxy-(1)]-6,7-benzomorphan.

20. The compound according to claim 1 which is 2-cyclopropylmethyl-5-ethyl-9-methyl-[1-acetoxy-2-methylpropoxy-(2)]-6,7-benzomorphan.

21. The compound according to claim 1 which is 2-cyclopropylmethyl-5-ethyl-9-methyl-2'-[4-acetoxy-2-methylbutoxy-(1)]-6,7-benzomorphan.

22. The compound according to claim 1 which is 2-cyclopropylmethyl-5-ethyl-9-methyl-2'-[4-propionyloxy-2-methylbutoxy-(1)]-6,7-benzomorphan.

23. The compound according to claim 1 which is 2-cyclopropylmethyl-5-ethyl-9-methyl-2'-[3-nicotinoyloxypropoxy-(1)]-6,7-benzomorphan.

24. The compound according to claim 1 which is 2-cyclopropylmethyl-5-ethyl-9-methyl-2'-[3-phenoxyacetoxypropoxy-(1)]-6,7-benzomorphan.

25. The compound according to claim 1 which is 2-cyclopropylmethyl-5-ethyl-9-methyl-2'-[3-N-ethoxycarbonyl-N-methyl-carbamoyloxypropoxy-(1)]-6,7-benzomorphan.

* * * * *